United States Patent [19]

Grim

[11] Patent Number: 4,852,557

[45] Date of Patent: Aug. 1, 1989

[54] SOFT-GOODS TYPE, FORMABLE ORTHOPAEDIC CAST

[75] Inventor: Tracy E. Grim, Tulsa, Okla.

[73] Assignee: Royce Medical Company, Culver City, Calif.

[21] Appl. No.: 198,152

[22] Filed: May 24, 1988

[51] Int. Cl.$^4$ .............................................. A61F 5/04
[52] U.S. Cl. ................................. 128/90; 128/87 R; 128/88; 128/89 R; 128/847; 128/846; 128/877; 128/878
[58] Field of Search .................. 128/90, 91, 402, D20, 128/77, 87 R, 89, 165, 877, 878, 881, 882, 846, 847

[56] References Cited

U.S. PATENT DOCUMENTS

| | | |
|---|---|---|
| 3,375,822 | 4/1968 | Rose . |
| 3,643,656 | 2/1972 | Young et al. . |
| 3,674,021 | 7/1972 | Snyder et al. ........................ 128/90 |
| 4,483,332 | 11/1984 | Rind . |
| 4,537,184 | 8/1985 | Williams, Jr. . |
| 4,683,877 | 8/1987 | Ersfeld et al. . |

*Primary Examiner*—Richard J. Apley
*Assistant Examiner*—N. Paul
*Attorney, Agent, or Firm*—Poms, Smith, Lande & Rose

[57] ABSTRACT

A foldable, wrappable envelope sleeve orthopedic cast immobilizes and conforms to the shape and configuration of a limb. The cast conforms to the limb through the use of airtight pouches which encapsulate open cell or fiberglass matrices impregnated with a water-activated urethane polymer. After the tightening of the cast around the limb, the injection of water into each pouch activates the urethane polymer which conforms to the configuration of the limb encased. Supplemental bendable ribs may be employed to splint the limb prior to activation of the hardenable material. The soft goods type cast is held in place by straps, and may be removed or adjusted by releasing or tightening the straps. The splinting elements may be removed and replaced.

29 Claims, 3 Drawing Sheets

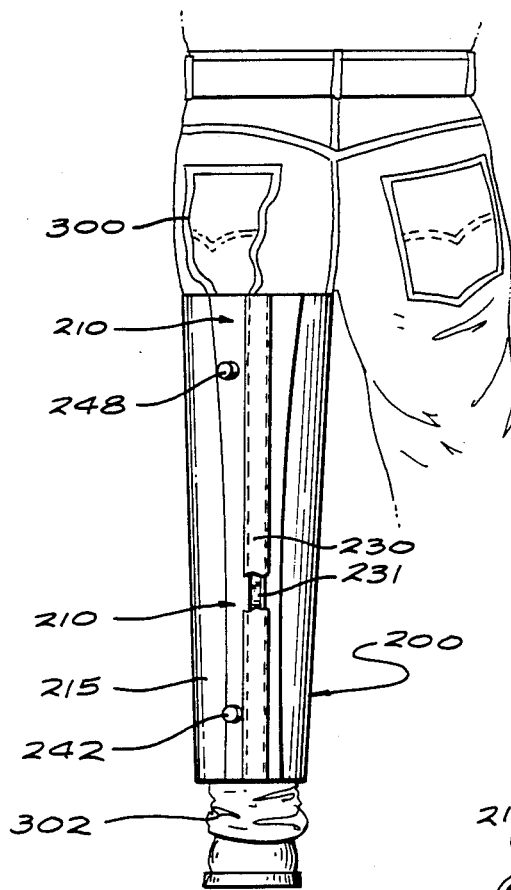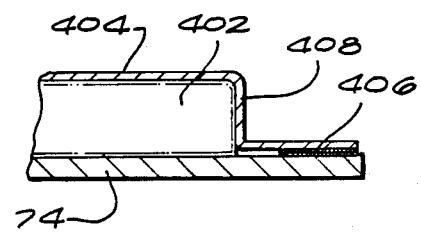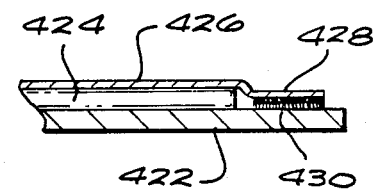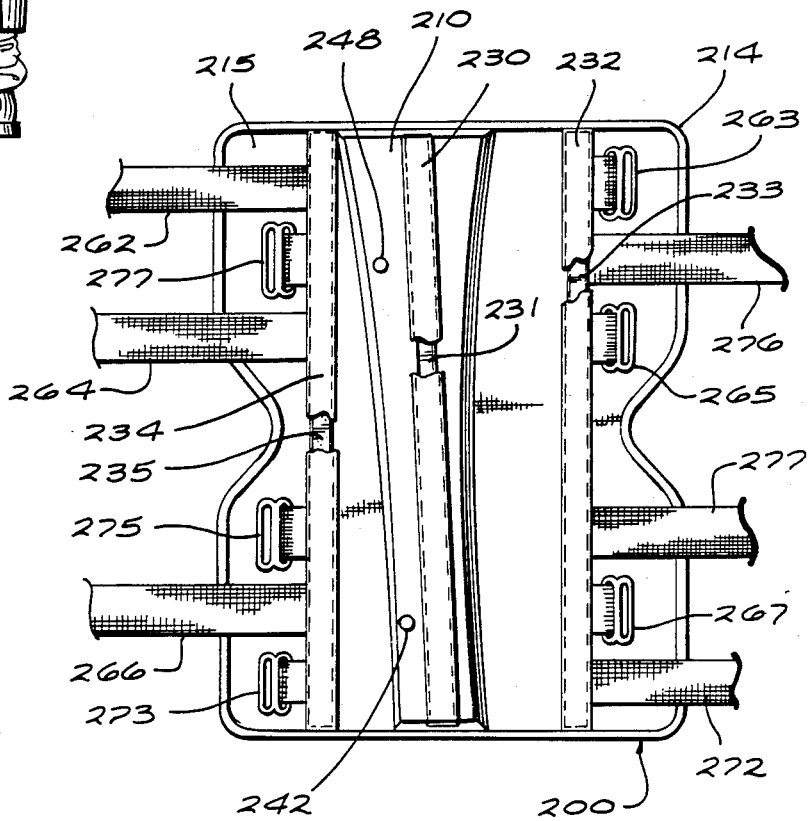

4,852,557

SOFT-GOODS TYPE, FORMABLE ORTHOPAEDIC CAST

FIELD OF THE INVENTION

This invention relates to methods of immobilizing body limbs or joints by using a lightweight, formable orthopaedic cast splint system.

BACKGROUND OF THE INVENTION

The traditional orthopaedic cast used bandages loaded with plaster of paris, which was then wrapped around the body limb which was injured or broken. The traditional plaster of paris cast is bulky, weighty and very uncomfortable for the wearer. Many techniques and systems have been proposed to either cut down on the weight, decrease the bulkiness or improve the comfort for the user. In addition, attempts have been made to design and make portable casts which are to be used at the site of an accidents for quick reaction to injuries. Certain casts and systems of this type are set forth in U.S. Pat. Nos. 3,375,822; 3,643,656; 4,483,332; 4,537,184, and 4,683,877. While in whole or in part these patented orthopedic cast systems have claimed lightweight or portability or an improved method as compared with plaster of paris casts, in fact, many have not lived up to their promise. In the cases noted above it appears that these cited references herein have reduced weight, but not comfort, or in many instances ease of use has been sacrificed. Also, none present the opportunity to remove the cast during use for cleansing the body limb, for comfort, and for improved X-ray examination.

Accordingly, principal objectives of the present invention are to provide an orthopedic cast and splint system which is lightweight, formable to the body limb and removable for ease of use. In accomplishing those needs, the invention will also increase the immobilization and stability of the limb to ensure the prevention of unneeded movements which could complicate healing.

SUMMARY OF THE INVENTION

The present invention provides a new and improved orthopedic cast which is foldable or wrappable and lightweight, which circumferentially conforms to the unique configuration of an individualized limb, and which is adjustable to accommodate limb swelling and muscle atrophy variations. The orthopedic cast has on its exterior surface or within the foam padding of its parallel material layers, a single or a plurality of formable pouches which encapsulate a water-activatable urethane impregnated matrix, formed of material such as an open cell foam, honeycomb material, fiberglass, Kevlar, carbonaceous fibers, or similar materials. The plastic pouch encloses unpolymerized urethane, which only begins polymerization upon the introduction of water.

In a broad aspect of the invention, the orthopaedic cast is similar to a soft goods type orthopaedic brace, including padding and straps for securing it to a limb or a joint. In addition, the cast has at least one elongated airtight pouch containing water-activated, hardenable material, such as urethane, in an open cell foam or in a fibrous matrix, and arrangements for applying the water to reach and activate the entire urethane impregnated material.

The cast wraps around a limb, for example, an arm. The cast surrounds the arm and through a securing fastening system, constrains and immobilizes the arm. The injury to the arm such as a break or severe sprain would need such immobilization to heal. As the wrappable, foldable and lightweight sleeve around the limb, the airtight pouches can initially conform to the limb configuration with bendable splint ribs to initially conform and immobilize the limb. Upon the secure tightening of the cast, the introduction of water into a single pouch or into multiple pouches will enable the urethane polymer to polymerize, harden and conform to the limb. While the time to inject the water into the pouch does not have to be immediately after the cast's application, it is contemplated that such injection would be within minutes of the setting of the injured limb and its immobilization within the cast.

The polymerization of the urethane improves the stability of the limb-case combination and prevents any movement which would interfere with healing. Upon the occurrence of an injury, the injured limb would be set and wrapped in the cast. The cast would be firmly secured about the limb, preferably with the use of strapping and Velcro pads. Upon completion of the cast's sleeve being tightly secured about the limb, each plastic foil pouch will have a predetermined amount of water injected by a syringe or other suitable technique. It is contemplated that each pouch or cast assembly could have a syringe associated with it for containing the amount of water necessary for polymerization. The syringe device could be for a one time use. With the syringe containing the necessary quantity of water, there would be no need for measuring the necessary water, which could result in too much or too little water being injected.

The pouches themselves should be airtight and moisture-proof, and may be constructed of multiple layers of materials, typically layers of plastic and metallic foil. These combinations would make the pouches structurally strong as well as airtight, with the plastic providing the strength and the foils being airtight. Within the pouches would be a one or more substrates or matrices impregnated with the water-activatable urethane polymer. Arrangements are provided for distributing the water from the inlet port to saturate and activate the entire matrix which is impregnated with the water activated hardenable material. This may be accomplished through the use of a distribution manifold or plenum separated by a perforated plastic sheet from the matrix, and with the sheet closer to the matrix and having larger holes, and a higher density of holes away from the inlet port, as compared with near the port. Alternatively, a tree type distribution channel with a series of branching channels may be provided.

The water is delivered into the pouch cavity by means of an inlet which may include a one-way valve. The water contacts the perforated plastic surface at a planar level closest to the inlet opening, and flows through the distribution volume, and the water then contacts the impregnated substrate or matrix initiating polymerization, by means of the holes in the plastic sheet. The holes in the plane closest to the water entry port are the smallest and the openings remote from the entry port and closest to the substrate surface are the largest. This arrangement is to ensure that water flows and contacts the substrate in a uniform manner. Alternatively, there could be a water delivery system wherein the entry port is coupled to tubes which break out in a tree fashion incorporated within the pouch so that small tubes extend to all areas of the matrix to ensure uniform contact with the impregnated matrix.

In accordance with additional aspects of the invention, the cast may be provided with bendable splint ribs of aluminum or plastic for initial holding of the limb while the water-activated hardenable material is being set up. It is also desirable that the pouches be maintained free of moisture, and this may be accomplished by manufacture in a dry environment, or by back-filling the airtight pouches with an inert gas, such as nitrogen. It is also noted that it is desirable that the cast systems be adjustable and removable, preferably by having hinge lines in the cast or using flexible sections of the soft goods assembly, and by the use of straps having Velcro securing arrangements. Further, both the pouches and the bendable splinting members may be mounted in removably closed elongated pockets in the soft goods cast assembly, so they may be removed and replaced as desired. The inlet port may have a threaded cap for resealing, and may be provided with a one-way valve. Alternatively, an input membrane may be used, with water being injected through the membrane by the needle of a medical syringe.

Other objects, features and advantages of the invention will become apparent from a consideration of the following detailed description and from the accompanying drawings.

BRIEF DESCRIPTION OF THE DRAWINGS

FIG. 6 illustrates an embodiment of the invention used on the left leg;

FIG. 7 is a detailed drawing of the soft goods cast of FIG. 6 shown in its unfolded configuration; and FIGS. 8 and 9 are cross-sectional views showing the removable nature of the splinting members.

DETAILED DESCRIPTION

Figure 1:
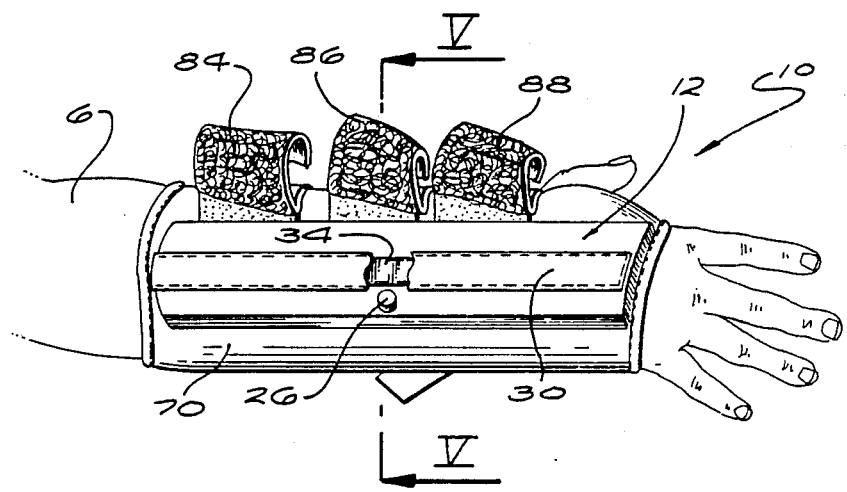
FIG. 1 is a perspective view of a soft goods type cast illustrating the principles of the current invention in use on the right forearm.
Figure 2:
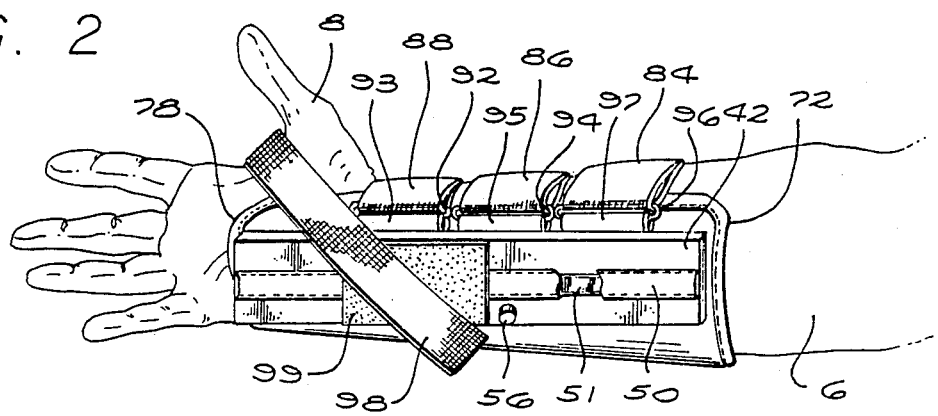
FIG. 2 is a perspective view of the orthopedic cast as seen from the inside of the right forearm.

Referring more particularly to the drawings, FIGS. 1 and 2 show the orthopedic cast 10 as it is used to immobilize the right forearm 6. FIG. 1 shows the back of the right forearm in a perspective view, with the cast 10 being mounted in place. In particular, it shows the pouch 12 wherein there is contained a water-activated hardenable urethane impregnated matrix. Water may be injected into the pouch through water inlet 6. The water activates the urethane polymer, which causes the elongated pouch to harden and conform to the shape of an individual's body limb upon the completion of the chemical reaction within pouch 12. Through the use of Velcro-covered straps 84, 86, 88, the cast 10 is firmly secured around the limb so that upon the introduction of water, the activated polymer hardens and takes a form or set providing a splint that conforms to the configuration of an individual's limb therein constrained.

Shown in FIG. 1 is splint rib assembly 30, which adds stability and can additionally be formed to the configuration of the arm and assist in the immobilization of the limb; and is particularly useful when the forearm is being initially set prior to the hardening of the urethane material. The splint rib assembly 30 can be a single splint rib 34 or a plurality of splint ribs. The splint rib 34 may be formed of a bendable strip of aluminum or a plastic strip having similar properties.

Figure 3:
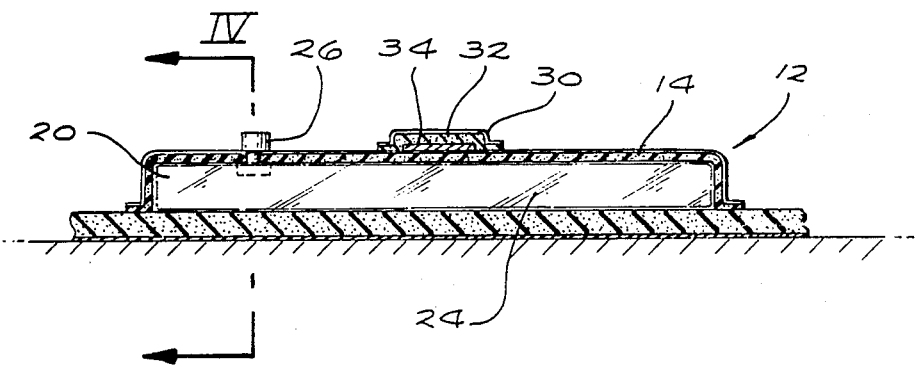
FIG. 3 is a cross-sectional view through an elongated pouch containing water activated hardenable material, and included in the soft goods type cast of FIGS. 1 and 2.
Figure 4:
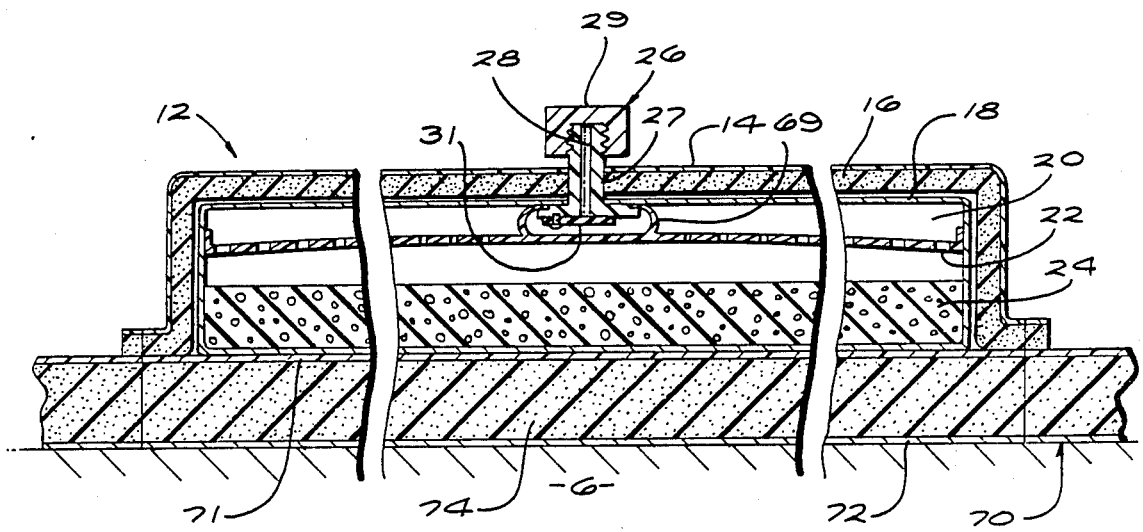
FIG. 4 is a cross-section through plane IV of FIG. 3, with a detailed showing of the pouch configuration.

FIG. 2 is a view of the cast 10 as seen from the inside of forearm 6. The cast 10 has two airtight pouches, 12 and 42, containing water-activated urethane impregnated substrates or matrices 24 (as shown in FIGS. 3 and 4). The inside forearm pouch 42 has a splint rib assembly 50, having a configuration which is substantially the same as the splint rib assembly 30 noted on the front forearm pouch 12, shown in FIG. 1, a water entry port 56 through which water is injected into the foil and plastic pouch 42 to activate the urethane polymer and a Velcro attachment pad 99.

For further immobilization, the strap 98 having Velcro attached thereto is swung through the hand 8 and attached to velcro pad 99. This further assists immobilization and securing of the soft goods splint in the desired position on the forearm. As shown in FIG. 2, there are hinged or pivotally mounted metal loops 92, 94, 96 through which the straps 84, 86, 88 loop to adjustably secure the cast circumscribably to the limb. The metal loops 92, 94, 96 are attached to the cast assembly by fabric loops 93, 95, 97. The cast body as indicated by reference numeral 70 in FIG. 1 is lined with foam material for comfort, and the unit is stitched closed around its circumferal edges with beads of fabric as indicated at reference numerals 76 and 78 in FIG. 2.

FIG. 3 shows a cross-section of the pouch 12 from an orientation perpendicular to the arm 6 and shows the aluminum splint rib 34 covered with vinyl covering and padding 32. The covering could also be a sheet of vinyl or other tear resistant fabric without any padding. The elongated pouch 12 has an outside covering of vinyl 14 which is impervious to water. Water is injected into the interior 20 of the pouch 12 through input port 26 to activate the water-activated urethane hardenable polymer so that the resultant splint conforms to the configuration of the limb to which it is applied.

FIG. 4 shows a detailed cross-section through Plane IV of the pouch of FIG. 3. The pouch 12 contains the substrate or matrix 24 impregnated with the water-activated urethane polymer. The pouch in which the impregnated substrate or matrix is enclosed, is mounted on the outer surface 71 of the cast sleeve 70. The interior of the pouch 20 contains substrate or matrix 24 impregnated with water-activated urethane polymer, and a substantially parallel apertured plastic sheet 22 which delivers a uniform water flow to activate the urethane polymer impregnated into matrix 24.

Inlet 26 has a removable cap 29 attachable to stem 27, with a water entry canal 28 contained therein. Optional one-way valving action may be provided by plastic flap 31. A water injecting means such as a syringe, is coupled to water canal 28 through which a pre-determined fixed quantity of water is injected, so that the water comes into contact with, and is distributed by, apertured plastic sheet 22. The predetermined quantity of water could be supplied by a syringe which would inject the requisite water into the pouch. Sheet 22 runs generally parallel to the surface of matrix 24. It is desirable that water applied to inlet port 26 be uniformly applied to the matrix 24 to activate and harden the entire urethane impregnation. To facilitate this action, the plastic sheet material 22, which need only be a few thousandths of an inch thick, may be slightly further from matrix 24 adjacent inlet port 26, and may have fewer and smaller holes near the port 26 than at the two remote ends of the pouch. The sheet plastic element 69 may block direct flow of water through sheet 22 and may also hold the adjacent portion of sheet 22 further away from matrix 24. Substrate or matrix 24 can be impregnated open cell foam, fiberglass, or any other suitable carrier material for the urethane polymer. A honeycomb structure or a matrix of Kevlar or other high strength fibers of the types used in sports gear, could also be employed, impregnated with water-activated hardenable material, and having an open configuration to receive the water for activation.

The pouch 12 is mounted on the surface 71 of the sleeve 70, on a surface opposite to that which contacts the surface of the limb. The pouch 12 has a surface of vinyl 14 which is impervious to water. Beneath that is padding 16, and beneath the layer of padding 16 is a composite layer 18 which may be formed of several layers of foil and plastic alternated with one another, which is impervious to water and which completely encapsulates the interior 20. The composite layer 18 is airtight. Underneath composite layer 18 is a thin perforated plastic sheet 22. Typically the foil included in layer 18 will be made out of metals which are non-reactive to the urethane chemical reactions. The pouch 12 is mounted on vinyl surface 71 which has padding 74 and which may have a thin tricot material layer 72 which engages the skin of the limb 6. This material will allow a certain amount of air to flow to the skin, and the tricot is soft to the touch. Between tricot surface 72 and foam 74 can be an additional layer of insulating material (not shown) to further protect the limb from any heat of reaction that could occur by the introduction of water into the foil pouch 12. While small pouches such as those that are used with an arm cast would normally not have a problem with heat reaction, some of the large embodiments such as that indicated in FIG. 6, for use on a leg, may generate sufficient heat which could cause discomfort to the wearer. In such cases, a protective insulated layer may be appropriate.

Figure 5:
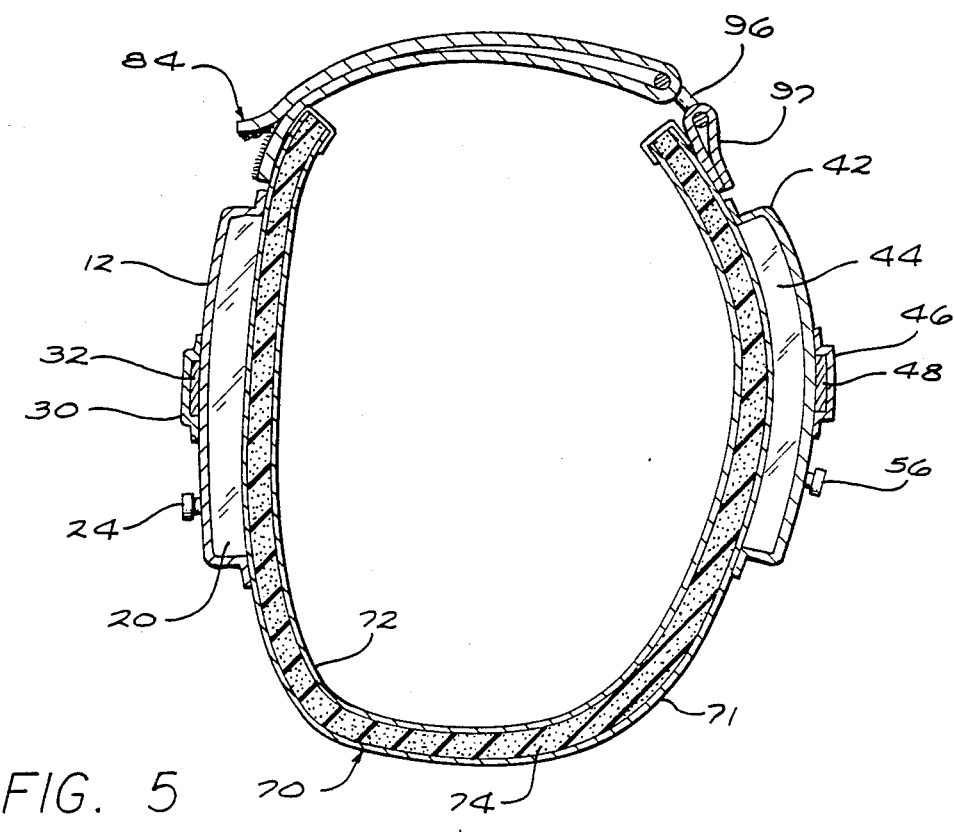
FIG. 5 is a view of the orthopedic cast in cross-section as it would appear on the right forearm.

FIG. 5 shows a cross-section of the soft goods cast as it would appear on the right forearm 6. The cross-sectional view shows two pouches 12 and 42 sitting approximately parallel to each other on the arm. FIG. 5 shows how the cast 10 takes the shape of the arm. Securing strap 84 loops through the strapping hinge loop 96. Cast 10 with exterior 71 which is made of vinyl or other water impervious material, padding 74, and interior 72, can be removed and replaced onto the arm to permit washing of the arm, and can be adjusted in size to accommodate changes in the arm involving reduction in swelling or slight muscle atrophy, for example.

Aluminum or bendable plastic splint ribs 32 and 48 can be made removable or permanent within the cast assembly. Additional rib members could be introduced on top of pouch 12 as well within the body of the cast 10 in areas below the foil pouches or in an area opposite to the velcro strapping within the padding area 74. In alternative embodiments, additional ribs can be added or removed depending on the severity of the injury to the limb or to obtain a desired degree of immobilization and stability. The splint ribs 32 and 48 are particularly helpful prior to water activation of the major splinting members in the pouch or pouches.

FIG. 6 illustrates the principles of the invention in use on the left leg. It runs from the ankle portion 302 to just below the left buttock at 300. Obviously, the cast itself will be much larger than that shown in FIGS. 1–5, and utilizes one long continuous pouch 210 which will have two entry ports 242 and 248 for the introduction of water, or there could be a plurality of individual smaller foil plastic pouches. A predetermined quantity of water is injected into water ports 242 and 248 of the pouch 210. Pouch 210 encapsulates a urethane impregnated substrate or matrix as noted above. For stability and immobilization, before activation of the water hardening material, there can be a single aluminum splint rib 231 which runs along the surface of the foil plastic pouch 210, or a plurality of aluminum splint ribs could be employed. The nature of the injury and constraint desired would determine the number of splint ribs.

The cast 200 is shown in more detail in FIG. 7, where it is shown in a flattened or unwrapped configuration. The strapping means shown could be secured by various means such as velcro, buckles, hooks, tying or any means to secure the cast around a limb. The number of securing belts utilized on cast 200 is indicated by strapping 262, 264, 266, 272, 274, 276 which have mating attaching metal loops 277, 275, 273, 267, 265, 263 where each is located opposite to the other. The number of securing straps can vary depending on the size of the limb or the degree of immobilization and stability desired or required. As noted previously, additional aluminum or plastic splint ribs can be introduced as shown in FIG. 7. Splint ribs 233, 231, 235, with mating vinyl pockets or padding which cover the splint ribs, can be added as needed. In the embodiment here shown, the splint ribs 231, 233, 235, and pouch 210 are permanent. In other instances, these ribs and the hardened urethane splint and pouch assemblies can be removable, as discussed below. The foil plastic pouch 210 has two water entry ports or valves 248 and 242 into which pre-determined amounts of water are injected for activation of the water-activated urethane, as noted above. The cast surface 215 on which the foil plastic pouch is mounted, can be of a waterproof material, typically of vinyl, or any other water impervious material. Underneath, the construction would be the same as shown above, with foam padding, tricot material, and with a stitched nylon lip 214 around the edge. The cast 200 has a cut-out to conform to the knee of the individual. Obviously, the cast will come in various sizes and have the necessary cut-outs for each limb or joint configuration. Also, the casts for legs, ankles, wrists, and the like will vary according to a person's size and age.

FIGS. 8 and 9 showed alternative arrangements at the ends of the splinting elements, so that they are removable. More specifically, with reference to FIG. 8, the padded base layer 74 has the airtight pouch assembly 402 mounted thereon, and secured in place by the outer elongated enclosing sleeve 404. At one end of the pouch 402, which becomes a splint when activated, the material of the sleeve 404 is removably secured to the base layer 74 by matching Velcro pads 406 which are on the inner surface of the end closure 408 of sleeve 404, and on the outer surface of base layer 74. Accordingly, if it is desired to change the splint configuration, due to a reduction in swelling of the limb, or for other medical reasons, the hardened splint pouch 402 may be removed, and a new one reinserted. For use with this type of removable pouch, a flush inlet port would be provided.

FIG. 9 shows a similar alternative arrangement for splinting stays, such as those shown at 233 and 235 in FIG. 7. More particularly, an underlying base member 422 may have an aluminum or bendable plastic splinting stay 424 secured to it by the flexible sleeve 426. The end closure 428 may be removably secured to the base member 422 by matching Velcro pads 430 so that the splinting stay 424 may be removed.

Thus, as indicated in FIGS. 8 and 9, the cast units of FIGS. 1–7 may be modified and adapted to different needs and conditions by selective removal and replacement of the splinting elements, either for the same patient and condition, or for different patients.

Incidentally, regarding the nature of the water hardenable material, it may be a urethane type material as described in U.S. Pat. Nos. 4,376,438; 4,433,680; 4,442,833; 4,502,479 and 4,683,877. It is available from W. R. Grace under their identification FHP2000. Other water hardenable materials could also be used.

It is to be understood that the foregoing description of the accompanying drawings shall relate to preferred and illustrated embodiments of the invention. Various modifications may be employed without departing from the sphere and the scope of the invention. Thus, by way of example and not limitation, instead of using foil plastic pouches on the surface of the cast, they could be incorporated within the cast material between the surfaces 72 and 71. In addition, the various ribs as indicated above can be removable and constructed of bendable plastic, which is similar to aluminum in its mechanical properties. There can be many tie systems and many configurations for the cast. Instead of layers of foil and plastic, a single layer of an impervious flexible material could be employed in the construction of the pouches. The use of a flexible wide zipper would have a different configuration than that illustrated; and overlapping Velcro covered portions on the fabric of the body of the soft goods cast could be used to hold the unit in place. Also, the configuration of the cast for an elbow would be much different than for a leg or a section of an arm. In addition, the orthopedic cast's function should not be limited to humans, but can be utilized on animals such domestic animals as dogs and cats, and for the use with farm animals, such as horses, cows and so forth. The veterinary uses as well as the medical uses of the invention are self-evident and are not to be limited in any way to a suggested specific animal or human use. Accordingly, the present invention is not limited to that precisely shown and described.

I claim:

1. A soft goods type orthopedic cast assembly comprising:
    a foldable or wrappable sleeve immobilizing means for circumscribingly immobilizing a body limb or joint;
    a water and air impervious elongated pouch encapsulating water permeable material impregnated with water-activated, hardenable material which structurally conforms to said limb when activated, said pouch being mounted as part of said immobilizing means;
    means for the external introduction of water into said elongated pouch to fully activate said water-activated hardenable material; and
    said immobilizing means including means for adjustably securing and releasing said immobilizing means to permit selective loosening and adjustment thereof while said assembly is resting on a support.

2. An orthopedic cast assembly as defined in claim 1 wherein said foldable or wrapping sleeve immobilizing means includes cushioning means for contacting said limb and for thermally protecting said limb from any heat of reaction of said water-activated hardenable material.

3. An orthopaedic cast assembly as defined in claim 1 wherein said means for introducing water includes a central entry point on the outer surface of said assembly and means for directing water to contact the entire contents of said pouch.

4. An orthopaedic cast assembly as defined in claim 1 wherein said assembly also has incorporated into it at least one bendable rib constituting means for acting as a splint in supporting and immobilizing said limb prior to activation of the hardenable material.

5. An orthopaedic cast as defined in claim 1 wherein said rib is removable secured to said cast.

6. An orthopaedic cast as defined in claim 1 wherein means are provided for removably mounting said pouch on said cast.

7. An orthopaedic soft goods type cast assembly comprising:
    a soft goods type support for extending at least two thirds of the way around an injured limb or a joint to be immobilized;
    said support including at least one elongated pouch containing a water permeable matrix impregnated with a water hardenable material;
    external port means for supplying water throughout the length of each said pouch to activate and harden said water hardenable material to splint the body limb or joint;
    adjustable straps for holding said soft goods type support in place;
    said soft goods type support, after hardening of said material, including flexible means for permitting bending of said assembly and loosening of said cast after said straps are loosened;
    said support being manufactured or initially formed or tailored specifically to fit a selected portion of the anatomy of a patient, and having an initial irregular contour or pattern which follows the irregular and unique shape of said selected portion of the anatomy;
    whereby said injured limb or joint may be initially set, and said cast may be subsequently adjusted by changing the tightness of the straps, and following partial healing, the cast may be removed or loosened under controlled conditions to permit washing, treatment or inspection of the skin, and said assembly may be subsequently replaced on the injured limb or joint to facilitiate full healing.

8. An assembly as defined in claim 7, wherein said water hardenable material is a urethane compound.

9. A cast assembly as defined in claim 7 including means for removable mounting said pouch onto said assembly.

10. A cast assembly as defined in claim 7 wherein said pouch is substantially airtight.

11. A cast assembly as defined in claim 10 wherein said pouch is filled with a moisture-free gas.

12. An orthopaedic cast assembly as defined in claim 7 wherein said straps extend less that half way around said assembly.

13. An orthopedic soft goods type cast comprising:

a soft goods type sleeve means for encompassing and immobilizing a body limb or joint, said sleeve means being elongated and having a generally U-shaped configuration for extending at least ⅔ of the way around said limb or joint;

said sleeve means including at least two separate elongated parts each having one edge foldably or hingedly secured to the other and Velcro type means for adjustably securing the other edge of said two parts together;

at least one of said parts including an elongated pouch containing a water permeable matrix impregnated with a water hardenable material;

external port means for supplying water throughout the length of each of said pouches to activate and harden said water-hardenable material to splinting said body limb or joint; and adjustable splinting means for providing an initial configuration of said sleeve means prior to the application of water to said water hardenable material;

whereby said limb may be initially oriented and set using said adjustable splinting means and said straps, and said hardenable material provides rigid long-term splinting protection for said limb, while still permitting removal of said cast for washing and inspection of the limb or the like, under controlled conditions following initial knitting of the bone or initial mending of the injury.

14. An assembly as defined in claim 13, wherein said water hardenable material is a urethane compound.

15. A cast assembly as defined in claim 13 including means for removably mounting said pouches onto said assembly.

16. A cast assembly as defined in claim 13 wherein said pouch is substantially airtight.

17. A cast assembly as defined in claim 13 further comprising an external water inlet and distribution means associated with said pouch for fully wetting said water hardenable material.

18. An orthopaedic soft goods type cast assembly comprising:

a soft goods type support for extending at least two thirds of the way around an injured limb or a joint to be immobilized;

said support including at least one elongated pouch containing a water permeable matrix impregnated with a water hardenable material;

means for supplying water throughout the length of each said pouch to activate and harden said water hardenable material to splint the body limb or joint;

adjustable straps for holding said soft goods type support in place;

said soft goods type support, after hardening of said material, including flexible means for permitting removal of said cast after said straps are loosened; and said pouch being formed of successive layers of foil and plastic;

whereby said injured limb or joint may be initially set, and said cast may be subsequently adjusted by changing the tightness of the straps, and following partial healing, the cast may be removed under controlled conditions to permit washing, treatment or inspection of the skin, and said assembly may be subsequently replaced on the injured limb or joint to facilitiate full healing.

19. An orthopaedic soft goods type cast assembly comprising:

a soft goods type sleeve means for encompassing an immobiling a body limb or joint, said sleeve means being elongated and having a generally U-shaped configuration;

said sleeve means including at least two separate elongated parts each having one edge foldably or hingedly secured to one another, and straps for adjustably securing the other edge of each of said two parts together;

at least one of said parts including an elongated pouch containing a water permeable material impregnated with a water hardenable material;

means for supplying water throughout the length of each of said pouches to activate and harden said water-hardenable material to splint said body limb or joint;

adjustable splinting means for providing an initial configuration of said sleeve means prior to the application of water to said water hardenable material; and said pouch being formed of successive layers of foil and plastic;

whereby said limb may be initially oriented and set using said adjustable splinting means and said straps, and said hardenable material provides rigid long-term splinting protection for said limb, while still permitting removal of said cast for washing and inspection of the limb or the like, under controlled conditions following initial knitting of the bone or initial mending of the injury.

20. An orthopaedic soft goods type cast assembly comprising:

a casing for enclosing a limb or the like and having a substantially U-shaped cross-section, and a substantial longitudinal extent;

a plurality of strap means each having at least one end fixedly secured to said casing for intercoupling the two outer edges of said casing and securing said casing onto a limb or the like with adjustable tension in said strap means;

a water and air impervious elongated pouch encapsulating water permeable material impregnated with water-activated, hardenable material which structurally conforms to said limb when activated, said pouch being mounted to and secured to conform with the configuration of said casing;

means for the introduction of water into said elongated pouch from outside of said assembly to activate said water-activated, hardenable material;

means for removably mounting said pouch and contents to said casing; and means including bendable ribs separate from said pouch and its contents, and securted to said casing, for providing initial splinting and partial immobilization of said limb prior to activation of said hardenable material.

21. An orthopaedic soft goods type cast assembly as defined in claim 20 wherein said straps include Velcro type material for adjustable securing said straps to hold said casing onto the limb.

22. An orthopaedic soft goods type cast assembly as defined in claim 20 wherein loops are secured to said casing adjacent at least one edge thereof for receiving said strap means.

23. An orthopaedic soft goods type cast assembly as defined in claimed 20 wherein said water-activated hardenable material is a urethane polymer.

24. An orthopaedic soft goods type cast assembly comprising:
- a casing for enclosing a limb or the like and having a substantially U-shaped cross-section, and a substantial longitudinal extent;
- a plurality of strap means each having at least one end fixedly secured to said casing for intercoupling the two out edges of said casing and securing said casing onto a limb or the like with adjustable tension in said strap means;
- a water and air impervious elongated pouch encapsulating water permeable material impregnated with water-activated, hardenable material which structurally conforms to said limb when activated said pounch being mounted to and secured to conform with the configuration of said casing; and
- means including bendable ribs separate from said pouch and its contents, and secured to said casing, for providing initial splinting and partial immobilation of said limb prior to activation of said hardenable material.

25. An orthopaedic soft goods type cast assembly comprising:
- a casing for enclosing a limb or the like and having a substantially U-shaped cross-section, and a substantial longitudinal extent;
- a plurality of strap means each having at least one end fixedly secured to said casing for intercoupling the two outer edges of said casing and securing said casing onto a limb or the like with adjustable tension in said strap means, said strap means only extending part of the way around said casing;
- a water and air impervious elongated pouch encapsulating water permeable material impregnated with water-activated, hardenable material which structurally conforms to said limb when activated, said pouch being mounted to and secured to conform with the configuration of said casing;
- means for the external introduction of water into said elongated pouch to fully activate said water-activated, hardenable material; and
- means for removably mounting said pouch and contents to said casing.

26. A cast assembly as defined in claim 24 including means for removably mounting said bendable splint members onto said support.

27. An orthopaedic soft goods type cast assembly comprising:
- a casing for enclosing a limb or the like and having a substantially U-shaped cross-section, and a substantial longitudinal extent;
- a plurality of strap means each having at least one end fixedly secured to said casing for intercoupling the two outer edges of said casing and securing said casing onto a limb or the like with adjustable tension in said strap means, said strap means only extending part of the way around said casing;
- a water and air impervious elongated pouch encapsulating a liquid permeable material impregnated with an activatable, hardenable material which structurally conforms to said limb when activated, said pouch being mounted to and secured to conform with the configuration of said casing;
- means for the external introduction of activating liquid into said elongated pouch to activate said activatable material;
- means for removably mounting said pouch and contents to said casing; and
- means including bendable ribs separate from said pouch and its contents, and secured to said casing, for providing initial splinting and partial immobilization of said limb prior to activation of said hardenable material.

28. An orthopaedic soft goods type cast assembly comprising:
- a soft goods type sleeve means for encompassing and immobilizing a body limb or joint, said sleeve means being elongated and having a generally U-shaped configuration;
- said sleeve means including at least two separate elongated parts each having one edge foldable or hingedly secured to one another, and means for adjustably securing the other edge of each of said two parts together, said adjustable securing means extending for a limited distance only comprising less than half the distance around the cast assembly;
- each of said part including an individual, separate elongated pouch containing a water permeable material impregnated with a water hardenable material; and
- means for supplying water throughout the length of each of said pouches to activate and harden said water-hardenable material to splint said body limb or joint;
- whereby said hardenable material provides rigid longterm splinting protection on tow sides of said limb, while still inspection of the limb or the like, under controlled conditions following initial knitting of the bone or initial mending of the injury.

29. An orthopaedic soft goods type cast assembly comprising:
- a casing for enclosing a limb or the like having a substantial longitudinal extent and opposed longitudinal edges;
- said casings being manufactured or initially formed or tailored specifically to fit a selected portion of the anatomy of a patient, and having an initial irregular contour or pattern which follows the irregular and unique shape of said selected portion of the anatomy;
- means for holding the two outer edges of said casing toward one-another and securing said casing onto a limb or the like adjustably to accommodate variations in swelling of the limb;
- a water and air impervious elongated pouch encapsulating a liquid permeable material impregnated with an activable, hardenable material which structurally conforms to said limb when activated, said pouch being mounted to and secured to conform with the configuration of said casing; and
- means for the introduction of activating liquid into said liquid permeable material to activate said activatable material.

* * * * *